(12) United States Patent
Gedrick et al.

(10) Patent No.: US 11,648,339 B1
(45) Date of Patent: May 16, 2023

(54) ZEN ROLLER

(71) Applicant: Zen Roller LLC, Santa Barbara, CA (US)

(72) Inventors: Dana Gedrick, Santa Barbara, CA (US); Nick E Oneill, Santa Barbara, CA (US)

(73) Assignee: Zen Roller LLC, Santa Barbara, CA (US)

( * ) Notice: Subject to any disclaimer, the term of this patent is extended or adjusted under 35 U.S.C. 154(b) by 469 days.

(21) Appl. No.: 16/602,717

(22) Filed: Nov. 26, 2019

Related U.S. Application Data

(60) Provisional application No. 62/766,053, filed on Oct. 1, 2018.

(51) Int. Cl.
*A61H 15/00* (2006.01)
*A61L 31/02* (2006.01)
*A61L 31/16* (2006.01)

(52) U.S. Cl.
CPC ........ *A61L 31/028* (2013.01); *A61H 15/0092* (2013.01); *A61L 31/16* (2013.01); *A61H 2201/1683* (2013.01); *A61L 2300/102* (2013.01)

(58) Field of Classification Search
None
See application file for complete search history.

(56) References Cited

U.S. PATENT DOCUMENTS

2018/0161234 A1* 6/2018 Dominee ............... A61H 15/00

OTHER PUBLICATIONS

Words of Wellness publication (elements massage®, Words of Wellness, The Benefits of Using Himalayan Salt Stones in Massage, Oct. 10, 2017).*

* cited by examiner

*Primary Examiner* — H. Sarah Park
(74) *Attorney, Agent, or Firm* — SoCal IP Law Group LLP; Steven C. Sereboff

(57) ABSTRACT

Zen Roller is manufactured to our exact specifications so the Himalayan salt barrel does not break during machining or use. The other two pieces (a surgical steel clasp, and a handle) are designed to hold the barrel while allowing for rotation—and for easy removal and/or replacement. In addition, the outer surface of the Himalayan salt barrel is highly polished to our exact specifications so it is non-abrasive to the skin.

7 Claims, 6 Drawing Sheets

The Zen Roller Small for the Face
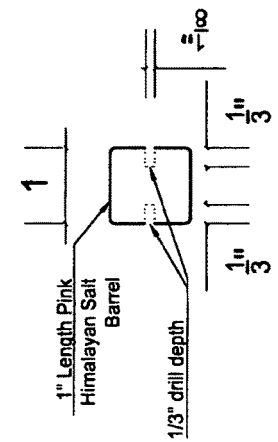
Side View
FIG. 1A
Front View
FIG. 1B
Himalayan Salt Barrel 101
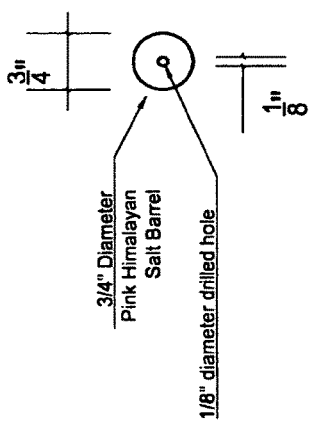
FIG. 1C  102
Steel Clasp
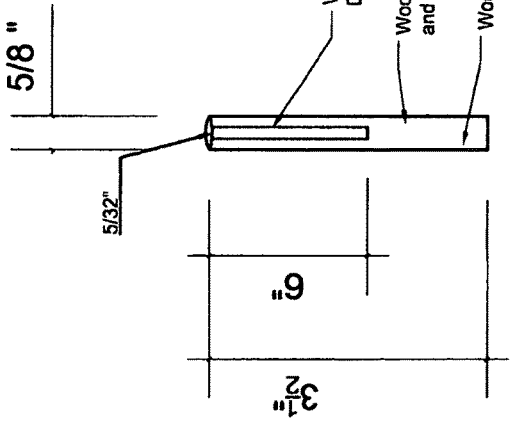
FIG. 1D  103  Wood Handle
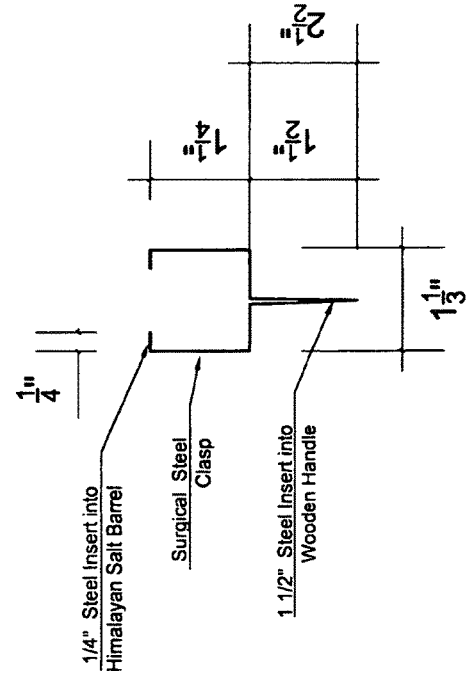

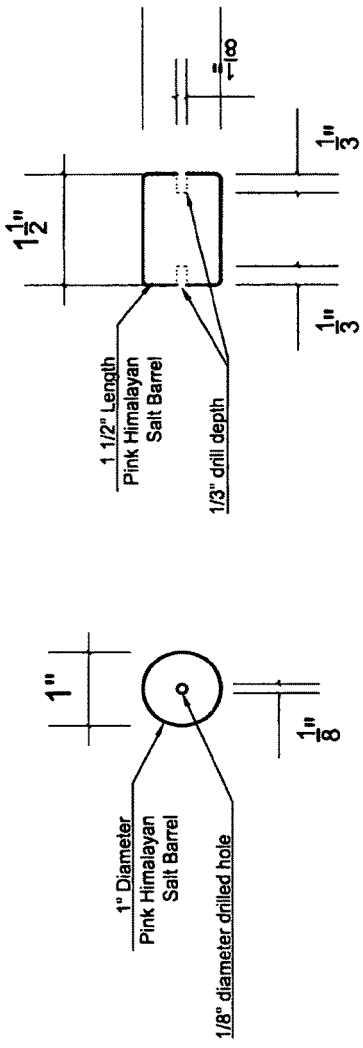
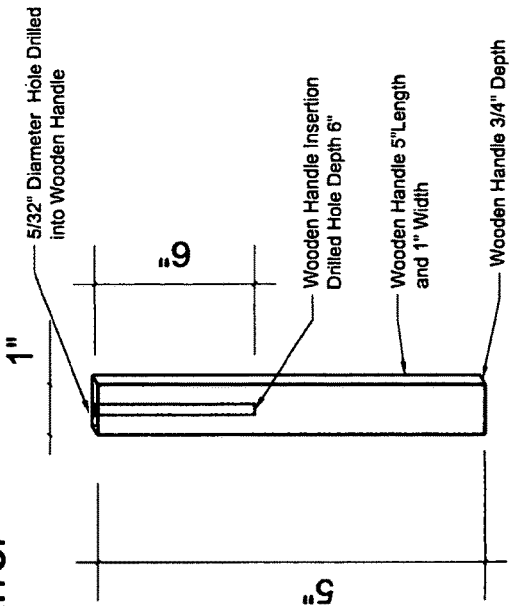
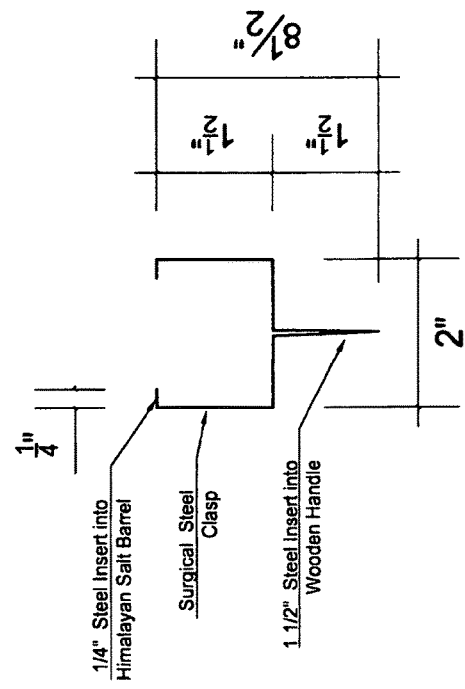

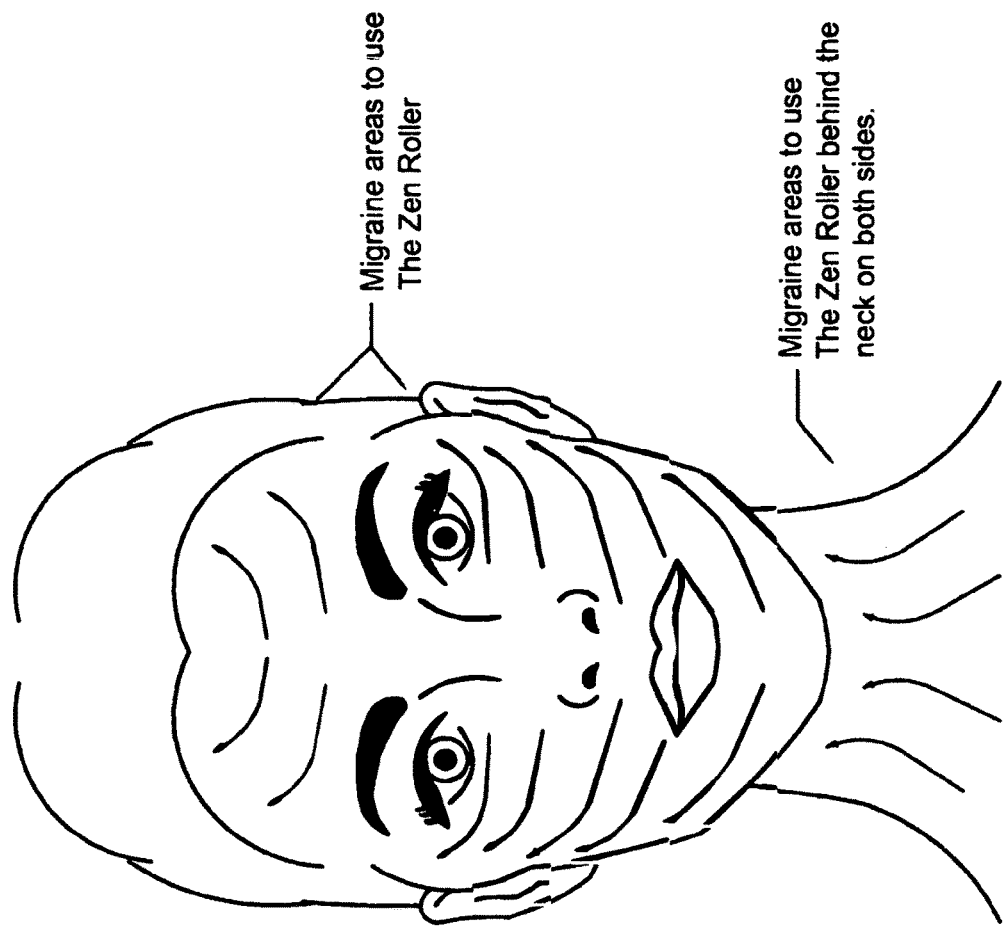

| Type of Materials | Stainless Steel Wire |   | Invoice No. | RSW/17/483 |
|---|---|---|---|---|
| Qty | 1223 lbs. |   | Date | 8/18/2017 |
| No. of Coils | 5 Coils |   | Order No. | 71241-1 |
| Type / Grade | 302 ASTM A313-13 |   | Date | 8/14/2017 |
| Size | 0.0915" |   |   |   |
| Tolerance | +/-0.0007" |   |   |   |

The wire supplied as per the details given above have been tested and found to satisfy requirements of your specification.

| CHEMICAL COMPOSITION | %C | %Mn | %Si | %S | %P | %Ni | %Cr | %Mo | %Cu | %N |
|---|---|---|---|---|---|---|---|---|---|---|
| Min |   |   |   |   |   | 8.00 | 17.00 |   |   |   |
| Max | 0.12 | 2.00 | 1.00 | 0.030 | 0.045 | 10.00 | 19.00 |   |   | 0.1000 |
| Actual | 0.078 | 1.32 | 0.39 | 0.002 | 0.025 | 8.05 | 18.61 | 0.10 | 0.35 | 0.0408 |

HEAT NO: RX - 11972

MECHANICAL PROPERTIES

| Coil. No. | Dia [Inch] | Tensile Strength [KSI] | Cast Helix | Surface Finish |
|---|---|---|---|---|
| MIN | 0.0908" | 238 |   |   |
| MAX | 0.0922" | 268 |   |   |
| 1 | 0.0913' | 247.51 | Good | SOAP COATED |

Note: This material is under ROHS Compliance

Steel Clasp Specifications

FIG. 4

ZEN ROLLER

Zen Roller devise is comprised of three engineered components; a barrel-shaped piece machined from pink Himalayan salt from Khewra, Pakistan, a surgical steel clasp, and a handle. These three components are designed to be assembled and disassembled easily so the barrel-shaped piece can rotate and be removed and replaced.

BACKGROUND

Zen Roller is the first wellness roller made with Himalayan salt crystal mined in Khewra, Pakistan. The Himalayan salt crystal is difficult to machine into a cylindrical barrel with a hole drilled through the length of the barrel. The crystalline structure is very prone to cracking and fracturing during machining.

In addition, the Himalayan salt crystal is naturally abrasive and can irritate and scratch the epidermis without a high-polish machined finish.

BRIEF SUMMARY OF INVENTION

By machining the Himalayan salt barrel to our exact specifications we created shallow holes on both sides for the steel clasp to hold and allow for rotation. We engineered these exact specifications because Himalayan salt crystal breaks easily and broke when a hole was drilled through the entire length of the barrel.

In addition, the outer surface of the barrel is polished to our specifications so it becomes a smooth surface that is non-abrasive to the skin.

The disclosed exemplary embodiments provide a device in which a Himalayan salt roller is created. In combination with two other parts, a surgical steel clasp and handle, the Zen Roller embodiment is complete (see FIG. 1 and FIG. 2).

Himalayan salt is difficult to work with and has never been carved into a barrel for use as a roller, but is commonly shaped into lamps and other products.

We drafted and sent detailed drawings (see pages 2/6 and 4/6), and a carved 3-dimensional cylindrical wooden model of the barrel, to the manufacturer in Pakistan. Several iterations took place over 6 months before the barrel was perfected.

The clasp material, surgical steel, was chosen because Himalayan salt is corrosive and surgical steel is non-reactive. The clasp design allows for of the barrel to be removed and/or replaced from the Zen Roller (see FIG. 1 and FIG. 2). The barrel then can be heated in the microwave, chilled in the refrigerator, or replaced when necessary.

The handle is designed with a hole in the middle for the clasp to insert and hold the barrel in place while it rotates (see FIG. 1 and FIG. 2)

Zen Roller is designed for use on the face and body (see page 5/6).

BRIEF DESCRIPTION OF DRAWINGS

FIG. 1A illustrates a side view of the small salt barrel.
FIG. 1B illustrates a front view of the small salt barrel.
FIG. 1C illustrates the steel clasp.
FIG. 1D illustrates the wood handle.
FIG. 2A illustrates a side view of the large salt barrel.
FIG. 2B illustrates a front view of the large salt barrel.
FIG. 2C illustrates the steel clasp.
FIG. 2D illustrates the wood handle.
FIG. 3 illustrates a view of a face.
FIG. 4 illustrates a steel clasp specification

DETAILED DESCRIPTION

Figure 1:
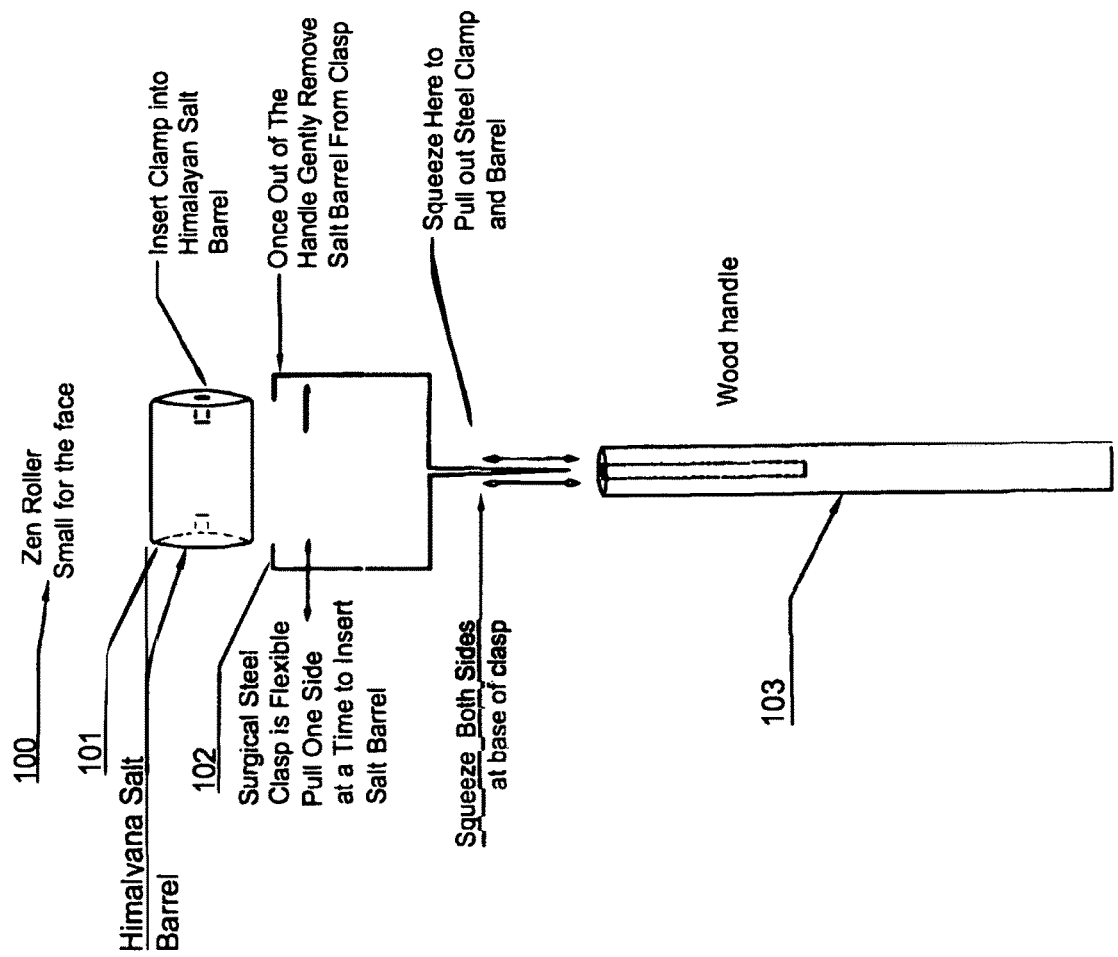
FIG. 1 illustrates a top view of the roller.

The first embodiment of the Zen Roller device has a small diameter barrel for use on the face and is illustrated in FIG. 1. The Zen Roller 100 comprises a Himalayan salt barrel 101 with steel clasp 102 to hold the removable barrel in the handle 103.

Figure 2:
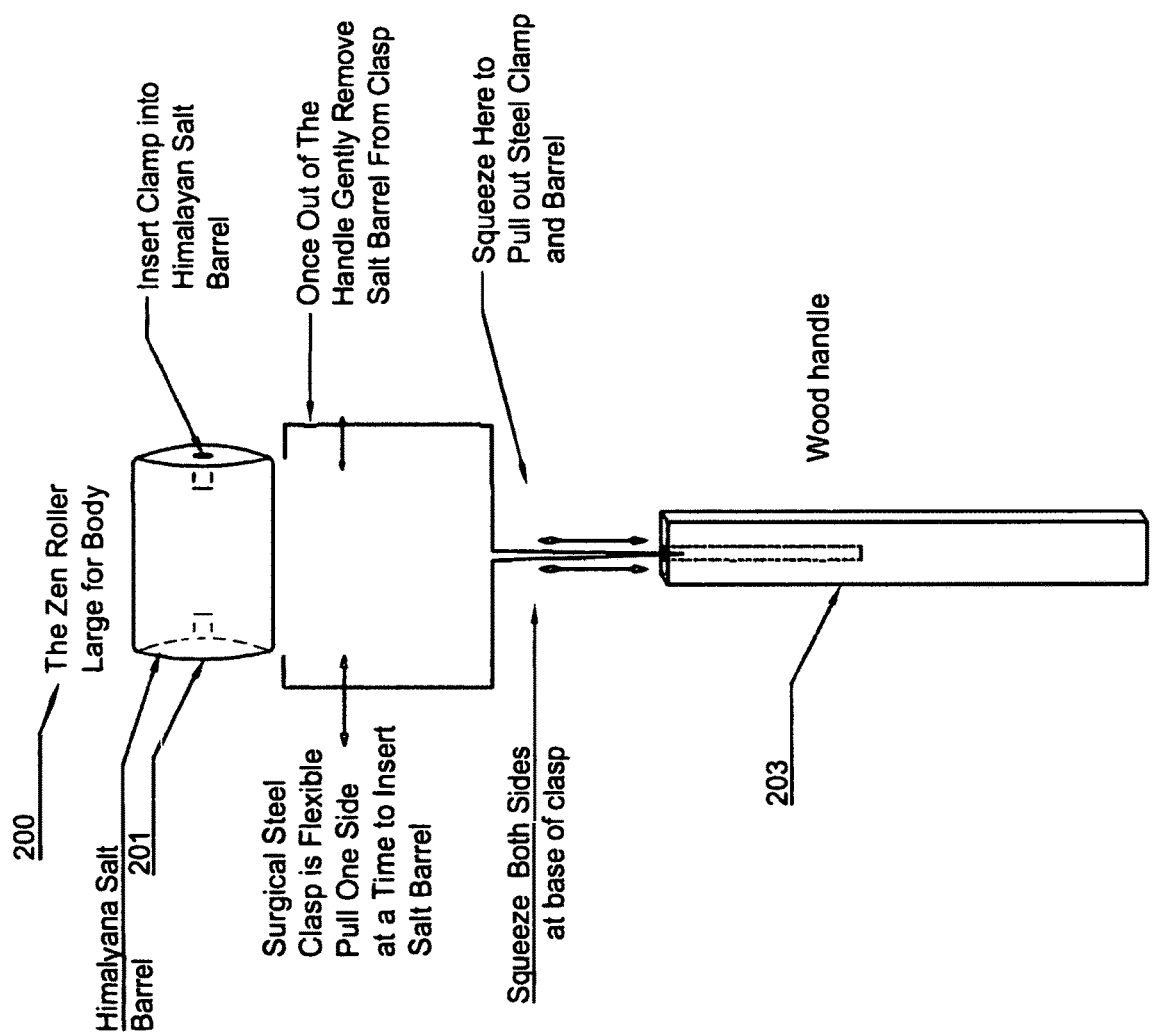
FIG. 2 illustrates a top view of the roller.

The second embodiment of the Zen Roller device has a large diameter barrel for use on the body and is illustrated in FIG. 2. The Zen Roller 200 comprises a Himalayan salt barrel 201 with steel clasp 202 to hold the removable barrel in the handle 203.

FIG. 1 and FIG. 2. Specifications were engineered to eliminate the inherent difficulty of working with Himalayan salt crystalline structure because it is prone to cracking and also has corrosive properties. Surgical steel was chosen as the ideal clasp material, specifications on detail page 6/6.

The Zen Roller is comprised of three components; Himalayan salt crystal, surgical steel clasp, and a handle. This is the only mineral roller made for the body and the face that is created with the Himalayan salt crystals. See FIG. 3 for how to use.

Zen Roller for the Face:

Anti-inflammatory great for under the eyes! May help fine lines and wrinkles in six months. Helps with reducing inflammation around the eye area.

Directions: Remove barrel from roller, chill in the refrigerator or freezer, re-insert barrel into clasp and handle. Roll on face and eye area for two minutes (see FIG. 3) Rinse face and pat dry. Wait ~1-5 minutes and then continue with your usual face routine. Always roll away from the center of your face in a gentle upward direction.

ZenRoller for the Body:

The anti-inflammatory and detoxifying properties of the Himalayan Salt help to relieve sore muscles, heat barrel in the microwave. (microwave for ~20 to 30 seconds) re-insert barrel into clasp and handle. Roll out the tight muscles. Use chilled barrel for headaches and to reduce bruising.

Caution if allergic to Iodine please test on your wrist before using anywhere else on your face or body. If there is a reaction please don't use The Zen Roller Please avoid eyeballs and eyelids.

Zen Roller is designed for pain relief associated with inflammation and treatment of acne, skin rashes, and bruises.

The 39 minerals in the Himalayan Salt that have health benefits:

1. Calcium: Calcium is extremely important for the growth and strengthening of bones and teeth.
2. Hydrogen: It is vital for the production of an important energy source in the body named Adenosine Triphosphate. Hydrogen is the source of protons needed for the production of ATP.
3. Phosphorus: Well, this looks like a key component for your well-being. It is found in all the cells but mainly in bones and teeth. It enhances the utilization of B complex vitamins and is involved in communication between the cells and various enzymatic reactions. It is also responsible for the formation of DNA and RNA. It helps to make you feel energetic and ups your endurance game.
4. Nitrogen: Helps in the digestion of your food. Hence, helps in your overall growth.

5. Carbon: This is the basic building block. It helps in the formation of big biological molecules.
6. Oxygen: Yet another most important element. It helps in breaking down the sugars into carbon dioxide and water. Oxygen and glucose provide high amounts of chemical energy to vital organs like the heart, liver, and kidneys for their functioning.
7. Sodium: It helps in maintaining the body's acid-base balance by regulating the fluid balance in and out of the cells. It is also helpful with muscle contractions and nerve transmission. Sodium helps in transporting carbon dioxide and the production of hydrochloric acid. It helps in transporting amino acids into the bloodstream and to the body cells.
8. Fluoride: Remember the toothpaste advertisement that says it is rich in fluoride? Well, it is true! Fluoride is important for the formation and health of teeth as it helps in retaining calcium in the body.
9. Cadmium: It is responsible for active metabolic activities.
10. Palladium: It is basically a transporting element. It significantly improves the uptake of lipoic acid and affects the electrical potential of the cells positively.
11. Aluminum: Controls the actions of a small number of enzymes.
12. Chromium: It enhances insulin function which is essential for carbohydrate metabolism and regulates blood sugar level. Because of all this chromium happens to be a component of the essential glucose tolerance factor. It is also found to be helpful in regulating cholesterol levels and energy production in the body.
13. Nickel: It is believed by scientists that nickel affects cell membranes, hormones, and enzymes.
14. Arsenic: Known to be responsible for the functioning of the nervous system and growth.
15. Silicon: Helpful in the growth of hair, nails, and skin. It helps with the formation of connective tissues like ligaments and tendons. Also strengthens bones paired up with calcium.
16. Calcium: Calcium is extremely important for the growth and strengthening of bones and teeth.
17. Hydrogen: It is vital for the production of an important energy source in the body named Adenosine Triphosphate. Hydrogen is the source of protons needed for the production of ATP.
18. Phosphorus: Well, this looks like a key component for your well-being. It is found in all the cells but mainly in bones and teeth. It enhances the utilization of B complex vitamins and is involved in communication between the cells and various enzymatic reactions. It is also responsible for the formation of DNA and RNA. It helps to make you feel energetic and ups your endurance game.
19. Nitrogen: Helps in the digestion of your food. Hence, helps in your overall growth.
20. Carbon: This is the basic building block. It helps in the formation of big biological molecules.
21. Oxygen: Yet another most important element. It helps in breaking down the sugars into carbon dioxide and water. Oxygen and glucose provide high amounts of chemical energy to vital organs like the heart, liver, and kidneys for their functioning.
22. Sodium: It helps in maintaining the body's acid-base balance by regulating the fluid balance in and out of the cells. It is also helpful with muscle contractions and nerve transmission. Sodium helps in transporting carbon dioxide and the production of hydrochloric acid. It helps in transporting amino acids into the bloodstream and to the body cells.
23. Fluoride: Remember the toothpaste advertisement that says it is rich in fluoride? Well, it is true! Fluoride is important for the formation and health of teeth as it helps in retaining calcium in the body.
24. Cadmium: It is responsible for active metabolic activities.
25. Palladium: It is basically a transporting element. It significantly improves the uptake of lipoic acid and affects the electrical potential of the cells positively.
26. Aluminum: Controls the actions of a small number of enzymes.
27. Chromium: It enhances insulin function which is essential for carbohydrate metabolism and regulates blood sugar level. Because of all this chromium happens to be a component of the essential glucose tolerance factor. It is also found to be helpful in regulating cholesterol levels and energy production in the body.
28. Nickel: It is believed by scientists that nickel affects cell membranes, hormones, and enzymes.
29. Arsenic: Known to be responsible for the functioning of the nervous system and growth.
30. Silicon: Helpful in the growth of hair, nails, and skin. It helps with the formation of connective tissues like ligaments and tendons. Also strengthens bones paired up with calcium.
31. Vanadium: Helps by converting food into energy. Also helps with the proper formation of teeth and bones.
32. Lanthanum: It helps by filtering out phosphate from the body.
33. Gallium: It restricts the formations of interleukin-6 beta which causes inflammation.
34. Rubidium: Rubidium+ ions concentrates on the body's electrolytic fluid because our body mistakes them to be potassium ions.
35. Cobalt: An essential component of Vitamin B12, it helps with the production of red blood cells.
36. Indium: Helps with healthy mineralization and absorption of all the minerals by the body.
37. Iodine: Essential for thyroid function. Also regulates metabolism, energy production, and cellular oxidation.
38. Iron: Primarily it is important for the production of hemoglobin. Also helps with a healthy immune system.
39. Magnesium: Acts as a muscle relaxant. Vital for heart health and maintenance and repair of cells. It also helps with hormone regulation and metabolism of protein and nucleic acids. Other than these, there are many other Himalayan salt minerals that work together in bringing out a balanced and healthy human body. These are:
bromine, antimony, silver, ruthenium, rhodium tellurium, scandium, titanium, cesium, barium, lanthanum, cerium, praseodymium, samarium, europium, gadolinium, terbium, dysprosium, holmium, erbium, thulium, ytterbium, lutetium, hafnium, tantalum, tungsten, rhenium, osmium, iridium, platinum, gold, mercury, thallium, lead, bismuth, polonium, astatine, francium, radium, actinium, thorium, protactinium, rubidium, strontium, yttrium, zirconium, niobium uranium, tin, neptunium and plutonium.

The invention claimed is:
1. A massage apparatus comprising:
a barrel of uncracked Himalayan salt having a smooth surface that is non-abrasive to human skin, the barrel having two ends, wherein each end has a centrally disposed mounting hole;
a handle; and
a surgical steel clasp removably holding the barrel to the handle and having a pair of ends adapted to fit into the mounting holes of the barrel and forming an axis upon which the barrel is manually rollable.

2. The massage apparatus of claim 1 wherein:
the barrel has a diameter of ¾ inch and a length of 1 inch;
the mounting holes are ⅛ inch in diameter and ⅓ inch deep; and
the end portions of the clasp are ¼ inch long.

3. The massage apparatus of claim 1 wherein:
the barrel has a diameter of 1 inch and a length of 1½ inches;
the mounting holes are ⅛ inch in diameter and ⅓ inch deep; and
the end portions of the clasp are ¼ inch long.

4. The massage apparatus of claim 1 wherein the barrel has a diameter of ¾ inch and a length of 1 inch.

5. The massage apparatus of claim 1 wherein the barrel has a diameter of 1 inch and a length of 1½ inches.

6. The massage apparatus of claim 1 wherein:
the mounting holes are ⅛ inch in diameter and ⅓ inch deep; and
the end portions of the clasp are ¼ inch long.

7. The massage apparatus of claim 1 wherein the barrel has a hole extending its length between the mounting holes.

\* \* \* \* \*